US012597138B2

(12) United States Patent
Zhou

(10) Patent No.: US 12,597,138 B2
(45) Date of Patent: Apr. 7, 2026

(54) SYSTEMS AND METHODS FOR ANNOTATING TARGET IMAGES BASED ON FEATURES THEREIN AND SELECTED CANDIDATE SAMPLE IMAGES WITH ANNOTATIONS

(71) Applicant: WUHAN UNITED IMAGING HEALTHCARE CO., LTD., Wuhan (CN)

(72) Inventor: Ming Zhou, Wuhan (CN)

(73) Assignee: WUHAN UNITED IMAGING HEALTHCARE CO., LTD., Wuhan (CN)

( * ) Notice: Subject to any disclaimer, the term of this patent is extended or adjusted under 35 U.S.C. 154(b) by 299 days.

(21) Appl. No.: 18/523,820

(22) Filed: Nov. 29, 2023

(65) Prior Publication Data

US 2024/0177839 A1    May 30, 2024

(30) Foreign Application Priority Data

Nov. 30, 2022    (CN) .......................... 202211514112.X

(51) Int. Cl.
G06T 7/00          (2017.01)
G06V 10/44        (2022.01)
(Continued)

(52) U.S. Cl.
CPC ............ *G06T 7/0014* (2013.01); *G06V 10/44* (2022.01); *G06V 10/761* (2022.01); *G06V 20/70* (2022.01);
(Continued)

(58) Field of Classification Search
CPC ......... G06T 7/0014; G06T 2207/10132; G06T 2207/20081; G06T 2207/20084;
(Continued)

(56) References Cited

U.S. PATENT DOCUMENTS 9,020,246 B2 * 4/2015 Li ........................ G06F 18/214
382/209
11,322,256 B2 * 5/2022 Sati ....................... G16H 15/00
(Continued)

FOREIGN PATENT DOCUMENTS

CN        111242948 B  *  9/2020  ........... G06F 18/241
CN        113035325 A     6/2021
(Continued)

OTHER PUBLICATIONS

Adnan et al. "Automatic image annotation based on deep learning models: a systematic review and future challenges." IEEE Access, vol. 9, pp. 50253-50264 (Year: 2021).*
(Continued)

*Primary Examiner* — Scott A Rogers
(74) *Attorney, Agent, or Firm* — METIS IP LLC

(57)          ABSTRACT

Systems and methods for image annotation may be provided. Sample images and annotation information of each of the sample images may be obtained. Each of the sample images may include one or more annotations, and the annotation information of each of the sample images may relate to the one or more annotations included in the sample image. One or more candidate sample images may be selected from the sample images based on feature information of a target image to be annotated. Target annotation information of one or more target annotations to be added to the target image may be determined based on the annotation information of the one or more candidate sample images. The one or more target annotations may be added to the target image based on the target annotation information.

20 Claims, 5 Drawing Sheets

(51) Int. Cl.

| | |
|---|---|
| *G06V 10/74* | (2022.01) |
| *G06V 10/82* | (2022.01) |
| *G06V 20/70* | (2022.01) |
| *G16H 30/40* | (2018.01) |

(52) U.S. Cl.

CPC ... *G16H 30/40* (2018.01); *G06T 2207/10132* (2013.01); *G06T 2207/20081* (2013.01); *G06T 2207/20084* (2013.01); *G06V 10/82* (2022.01); *G06V 2201/03* (2022.01)

(58) Field of Classification Search

CPC ...... G16H 30/40; G06V 10/44; G06V 10/761; G06V 10/82; G06V 20/70; G06V 2201/03

See application file for complete search history.

(56) References Cited

U.S. PATENT DOCUMENTS

| | | | |
|---|---|---|---|
| 11,403,766 B2* | 8/2022 | Wei | G06T 7/174 |
| 11,961,226 B2* | 4/2024 | Xiao | G16H 30/20 |

| | | | | |
|---|---|---|---|---|
| 2018/0360427 | A1 | 12/2018 | Nakano et al. | |
| 2023/0077830 | A1* | 3/2023 | Quan | G06N 3/09 |
| | | | | 382/155 |
| 2024/0331418 | A1* | 10/2024 | Murozono | G06T 7/60 |
| 2025/0054322 | A1* | 2/2025 | Ye | G06F 40/279 |

FOREIGN PATENT DOCUMENTS

| | | | | |
|---|---|---|---|---|
| CN | 115410165 A | * | 11/2022 | |
| CN | 115544291 A | * | 12/2022 | G06V 10/462 |
| CN | 116758372 A | * | 9/2023 | |
| CN | 116935149 A | * | 10/2023 | G06N 3/04 |
| WO | 2021054752 A2 | | 3/2021 | |

OTHER PUBLICATIONS

Zhang et al. "A review on automatic image annotation techniques." Pattern Recognition, 45(1), pp. 346-362 (Year: 2012).*

\* cited by examiner

<u>100</u>

<u>400</u>

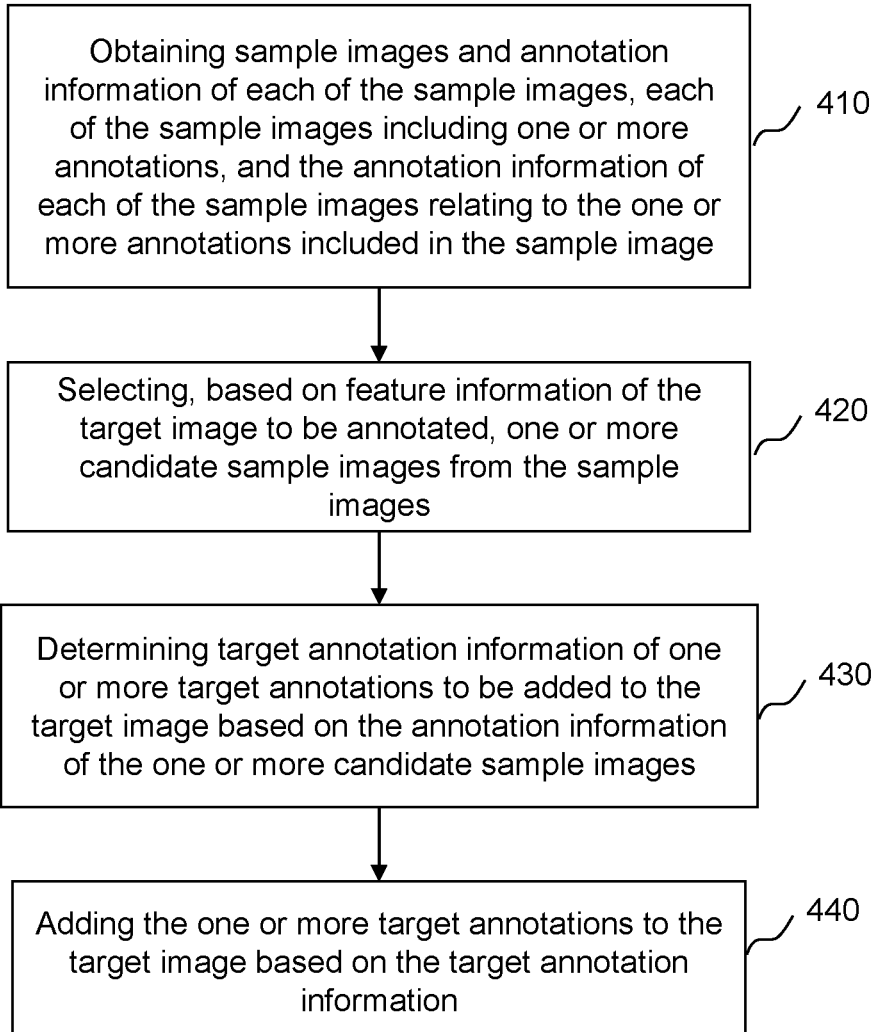

Obtaining sample images and annotation information of each of the sample images, each of the sample images including one or more annotations, and the annotation information of each of the sample images relating to the one or more annotations included in the sample image — 410

Selecting, based on feature information of the target image to be annotated, one or more candidate sample images from the sample images — 420

Determining target annotation information of one or more target annotations to be added to the target image based on the annotation information of the one or more candidate sample images — 430

Adding the one or more target annotations to the target image based on the target annotation information — 440

FIG. 4

500
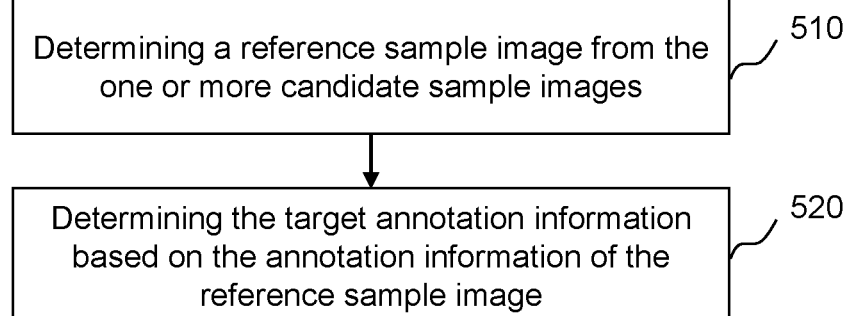
Determining a reference sample image from the one or more candidate sample images          510
Determining the target annotation information based on the annotation information of the reference sample image          520
FIG. 5

SYSTEMS AND METHODS FOR ANNOTATING TARGET IMAGES BASED ON FEATURES THEREIN AND SELECTED CANDIDATE SAMPLE IMAGES WITH ANNOTATIONS

CROSS-REFERENCE TO RELATED APPLICATIONS

This application claims priority of Chinese Patent Application No. 202211514112.X filed on Nov. 30, 2022, the contents of which are incorporated herein by reference.

TECHNICAL FIELD

The present disclosure relates to image annotation, and in particular, to image annotation for medical images.

BACKGROUND

Medical imaging technology has been widely used for generating medical images of interior of a patient's body for, e.g., clinical examinations, medical diagnosis, and/or treatment purposes. Usually, one or more annotations need to be added to the medical images manually by a user (e.g., a doctor), which is inefficient and susceptible to human error or subjectivity.

SUMMARY

According to an aspect of the present disclosure, a system for image annotation may be provided. The system may include at least one storage device including a set of instructions and at least one processor. The at least one processor may be configured to communicate with the at least one storage device. When executing the set of instructions, the at least one processor may be configured to direct the system to perform one or more of the following operations. The system may obtain sample images and annotation information of each of the sample images. Each of the sample images may include one or more annotations, and the annotation information of each of the sample images may relate to the one or more annotations included in the sample image. The system may also select one or more candidate sample images from the sample images based on feature information of a target image to be annotated. Further, the system may determine target annotation information of one or more target annotations to be added to the target image based on the annotation information of the one or more candidate sample images. Then, the system may add the one or more target annotations to the target image based on the target annotation information.

In some embodiments, to select one or more candidate sample images from the sample images based on feature information of a target image to be annotated, for each of the sample images, the system may determine a similarity degree between the sample image and the target image based on sample feature information of the sample image and the feature information of the target image. In response to determining that the similarity degree exceeds a threshold, the system may designate the sample image as one of the one or more candidate sample images.

In some embodiments, the sample images and the target image may be ultrasound images, the feature information may include one or more first operation parameters of a first ultrasound probe that collects the target image. The sample feature information of each sample image may include one or more second operation parameters of a second ultrasound probe that collects the sample image.

In some embodiments, to determine target annotation information of one or more target annotations to be added to the target image based on the annotation information of the one or more candidate sample images, the system may determine a reference sample image from the one or more candidate sample images. Further, the system may determine the target annotation information based on the annotation information of the reference sample image.

In some embodiments, the annotation information of each of the sample images may include an annotation number and/or an annotation time of each annotation included in the sample image. The reference sample image may be the candidate sample image that has the largest annotation number and/or the latest annotation time among the one or more candidate sample images.

In some embodiments, to determine a reference sample image from the one or more candidate sample images, for each of the one or more candidate sample images, the system may determine a reliability value of each annotation included in the candidate sample image based on the annotation information of the candidate sample image. Further, the system may determine the reference sample image based on the reliability value of each annotation in each of the one or more candidate sample images.

In some embodiments, to determine a reliability value of each annotation included in the candidate sample image based on the annotation information of the candidate sample image, for each annotation included in the candidate sample image, the system may obtain a priority of the annotation from an annotation library based on the annotation information of the candidate sample image. The annotation library may store annotations and their respective priorities. Further, the system may determine the reliability value of the annotation based on the priority of the annotation.

In some embodiments, the annotation information of the reference sample image may include annotation text and an annotation position of each annotation included in the reference sample image. To determine the target annotation information based on the annotation information of the reference sample image, for each of the one or more target annotations, the system may designate the annotation text of a corresponding annotation included in the reference sample image as an annotation text of the target annotation. Further, the system may determine an annotation position of the target annotation based on the annotation position of the corresponding annotation, a size of the reference sample image, and a size of the target image.

In some embodiments, the sample images and the target image may be ultrasound images, and to determine an annotation position of the target annotation, the system may determine one or more first operation parameters of a first ultrasound probe that collects the target image and one or more second operation parameters of a second ultrasound probe that collects the reference sample image. The system may also determine a pseudo image corresponding to the one or more first operation parameters based on the one or more first operation parameters and the one or more second operation parameters. Further, the system may determine a reference position in the pseudo image corresponding to the annotation position of the corresponding annotation. Then, the system may determine the annotation position of the target annotation based on the reference position, the size of the reference sample image, and the size of the target image.

In some embodiments, to add the one or more target annotations to the target image based on the target annotation information, the system may determine one or more verification sample images other than the reference sample image from the sample images based on the annotation information of each of the sample images and the target annotation information. Further, the system may verify whether the target annotation information satisfies a preset condition based on the one or more verification sample images. In response to determining that the target annotation information satisfies the preset condition, the system may add the one or more target annotations to the target image based on the target annotation information.

According to yet another aspect of the present disclosure, a method for image annotation may be provided. The method may include obtaining sample images and annotation information of each of the sample images. Each of the sample images may include one or more annotations, and the annotation information of each of the sample images may relate to the one or more annotations included in the sample image. The method may also include selecting one or more candidate sample images from the sample images based on feature information of a target image to be annotated. The method may also include determining target annotation information of one or more target annotations to be added to the target image based on the annotation information of the one or more candidate sample images. The method may further include adding the one or more target annotations to the target image based on the target annotation information.

According to yet another aspect of the present disclosure, a non-transitory computer readable medium may be provided. The non-transitory computer readable medium may include at least one set of instructions for image annotation. When executed by one or more processors of a computing device, the at least one set of instructions may cause the computing device to perform a method. The method may include obtaining sample images and annotation information of each of the sample images. Each of the sample images may include one or more annotations, and the annotation information of each of the sample images may relate to the one or more annotations included in the sample image. The method may also include selecting one or more candidate sample images from the sample images based on feature information of a target image to be annotated. The method may also include determining target annotation information of one or more target annotations to be added to the target image based on the annotation information of the one or more candidate sample images. The method may further include adding the one or more target annotations to the target image based on the target annotation information.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 4 is a flowchart illustrating an exemplary process for image annotation according to some embodiments of the present disclosure;

FIG. 5 is a flowchart illustrating an exemplary process for determining target annotation information according to some embodiments of the present disclosure.

DETAILED DESCRIPTION

Figure 1:
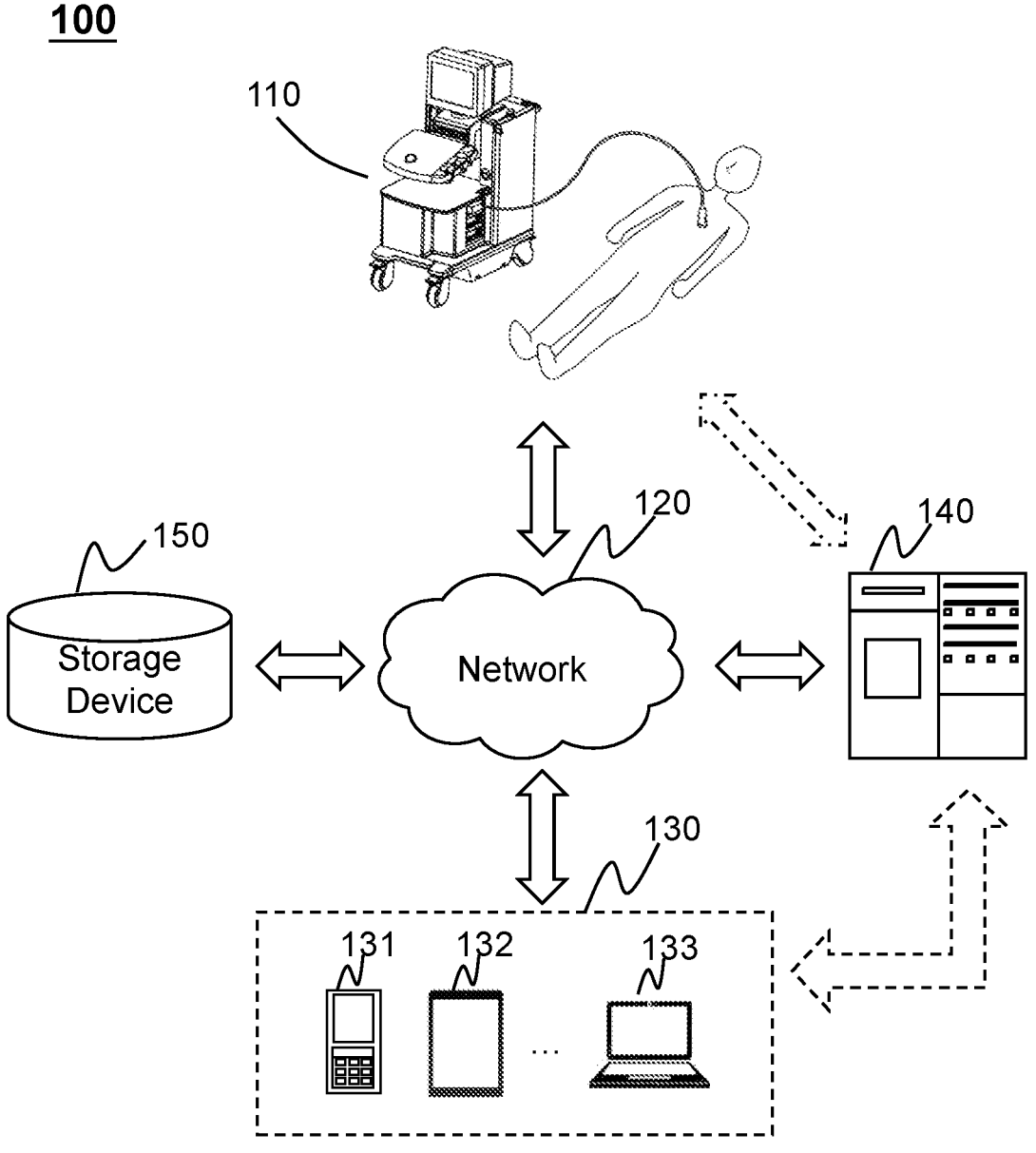
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "pixel" and "voxel" in the present disclosure are used interchangeably to refer to an element of an image. An anatomical structure shown in an image of a subject (e.g., a patient) may correspond to an actual anatomical structure existing in or on the subject's body. For example, a body part shown in an image may correspond to an actual body part existing in or on the subject's body, and a feature point in an image may correspond to an actual feature point existing in or on the subject's body. For the convenience of descriptions, an anatomical structure shown in an image and its corresponding actual anatomical structure are used interchangeably. For example, the chest of the subject refers to the actual chest of the subject or a region representing the chest in an image of the subject.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

In the present disclosure, a representation of a subject (e.g., an object, a patient, or a portion thereof) in an image may be referred to as "subject" for brevity. For instance, a representation of an organ, tissue (e.g., a heart, a liver, a lung), or an ROI in an image may be referred to as the organ, tissue, or ROI, for brevity. Further, an image including a representation of a subject, or a portion thereof, may be referred to as an image of the subject, or a portion thereof, or an image including the subject, or a portion thereof, for brevity. Still further, an operation performed on a representation of a subject, or a portion thereof, in an image may be referred to as an operation performed on the subject, or a portion thereof, for brevity. For instance, a segmentation of a portion of an image including a representation of an ROI from the image may be referred to as a segmentation of the ROI for brevity.

In conventional image annotation approaches, one or more annotations are manually added to a medical image by a user, which is inefficient and susceptible to human error or subjectivity. Thus, it may be desirable to develop automated image annotation systems and methods, thereby improving the annotation efficiency and the annotation accuracy. The terms "automatic" and "automated" are used interchangeably referring to methods and systems that analyze information and generate results with little or no direct human intervention.

An aspect of the present disclosure relates to systems and methods for image annotation. The systems may obtain sample images and annotation information of each of the sample images. Each sample image may include one or more annotations, and the annotation information of each sample image relates to the one or more annotations included in the sample image. The systems may select one or more candidate sample images from the sample images based on feature information of a target image to be annotated. The systems may also determine target annotation information of one or more target annotations to be added to the target image based on the annotation information of the one or more candidate sample images. Further, the systems may add the one or more target annotations to the target image based on the target annotation information.

Compared with the conventional image annotation approaches, the methods and systems of the present disclosure may be automatically implemented with reduced or minimal or without user intervention, which is more efficient (by, e.g., reducing the workload of a user and the time needed for the image annotation), more accurate, and insusceptible to human error or subjectivity.

FIG. 1 is a schematic diagram illustrating an exemplary medical system 100 according to some embodiments of the present disclosure. As shown in FIG. 1, the medical system 100 may include an imaging device 110, a network 120, one or more terminals 130, a processing device 140, and a storage device 150. In some embodiments, the imaging device 110, the terminal(s) 130, the processing device 140, and/or the storage device 150 may be connected to and/or communicate with each other via a wireless connection (e.g., the network 120), a wired connection, or a combination thereof. The connection between the components of the medical system 100 may be variable.

The imaging device 110 may be configured to scan a subject (or a part of the subject) to acquire medical image data associated with the subject. The subject may include a biological subject and/or a non-biological subject. For example, the subject may be a human being, an animal, or a portion thereof. As another example, the subject may be a phantom. In some embodiments, the subject may be a patient (or a portion thereof). The medial image data relating to the subject may be used for generating an anatomical image (e.g., a CT image, an MRI image, etc.) of the subject. The anatomical image may illustrate an internal structure of the subject. In some embodiments, the imaging device 110 may include a single-modality scanner and/or multi-modality scanner. The single modality scanner may include, for example, a magnetic resonance angiography (MRA) scanner, a computed tomography angiography (CTA) scanner, an X-ray scanner, a CT scanner, a magnetic resonance imaging (MRI) scanner, an ultrasonography scanner, a positron emission tomography (PET) scanner, a Digital Radiography (DR) scanner, or the like, or any combination thereof. The multi-modality scanner may include, for example, an X-ray imaging-magnetic resonance imaging (X-ray-MRI) scanner, a positron emission tomography-X-ray imaging (PET-X-ray) scanner, a single-photon emission computed tomography-magnetic resonance imaging (SPECT-MRI) scanner, a positron emission tomography-computed tomography (PET-CT) scanner, etc. In some embodiments, the imaging device 110 may be an ultrasonography scanner. It should be noted that the imaging device 110 described below is merely provided for illustration purposes, and is not intended to limit the scope of the present disclosure.

The network 120 may include any suitable network that can facilitate the exchange of information and/or data for the medical system 100. In some embodiments, one or more components of the medical system 100 (e.g., the imaging device 110, the processing device 140, the storage device 150, the terminal(s) 130) may communicate information and/or data with one or more other components of the medical system 100 via the network 120. For example, the processing device 140 may obtain image data from the imaging device 110 via the network 120.

The terminal(s) 130 may be connected to and/or communicate with the imaging device 110, the processing device 140, and/or the storage device 150. For example, the terminal(s) 130 may display an annotated target image. In some embodiments, the terminal(s) 130 may include a mobile device 131, a tablet computer 132, a laptop computer 133, or the like, or any combination thereof. In some embodiments, the terminal(s) 130 may be part of the processing device 140.

The processing device 140 may process data and/or information obtained from the imaging device 110, the storage device 150, the terminal(s) 130, or other components of the medical system 100. For example, the processing device 140 may obtain sample images and annotation information of each of the sample images. Further, the processing device 140 may add one or more target annotations to a target image based on the sample images and the annotation information of each sample image.

In some embodiments, the processing device 140 (e.g., one or more modules illustrated in FIG. 3) may execute instructions and may accordingly be directed to perform one or more processes (e.g., processes 400 and 500) described in the present disclosure. For example, each of the one or more processes may be stored in a storage device (e.g., the storage device 150) as a form of instructions, and invoked and/or executed by the processing device 140.

In some embodiments, the processing device 140 may be a single server or a server group. In some embodiments, the processing device 140 may be local to or remote from the medical system 100. Merely for illustration, only one processing device 140 is described in the medical system 100. However, it should be noted that the medical system 100 in the present disclosure may also include multiple processing devices. Thus operations and/or method steps that are performed by one processing device 140 as described in the present disclosure may also be jointly or separately performed by the multiple processing devices. For example, if in the present disclosure the processing device 140 of the medical system 100 executes both process A and process B, it should be understood that the process A and the process B may also be performed by two or more different processing devices jointly or separately in the medical system 100 (e.g., a first processing device executes process A and a second processing device executes process B, or the first and second processing devices jointly execute processes A and B).

The storage device 150 may store data, instructions, and/or any other information. In some embodiments, the storage device 150 may store data obtained from the processing device 140, the terminal(s) 130, and/or the imaging device 110. For example, the storage device 150 may store image data collected by the imaging device 110. As another example, the storage device 130 may store annotated medical images. In some embodiments, the storage device 150 may store data and/or instructions that the processing device 140 may execute or use to perform exemplary methods described in the present disclosure.

It should be noted that the above description of the medical system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the medical system 100 may include one or more additional components. Additionally or alternatively, one or more components of the medical system 100 described above may be omitted. As another example, two or more components of the medical system 100 may be integrated into a single component.

Figure 2:
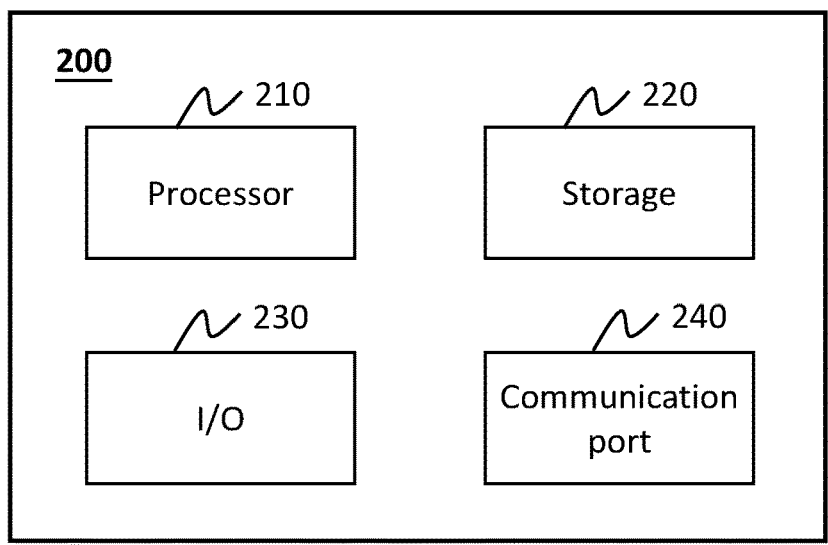
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device according to some embodiments of the present disclosure. In some embodiments, the processing device 140 may be implemented on the computing device 200. As illustrated in FIG. 2, the computing device 200 may include a processor 210, a storage 220, an input/output (I/O) 230, and a communication port 240.

The processor 210 may execute computer instructions (program code) and perform functions of the processing device 140 in accordance with techniques described herein. The computer instructions may include routines, programs, objects, components, signals, data structures, procedures, modules, and functions, which perform particular functions described herein. Merely for illustration purposes, only one processor is described in the computing device 200. However, it should be noted that the computing device 200 in the present disclosure may also include multiple processors, and thus operations of a method that are performed by one processor as described in the present disclosure may also be jointly or separately performed by the multiple processors.

The storage 220 may store data/information obtained from the imaging device 110, the terminal device 130, the storage device 150, or any other component of the PET system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure.

The I/O 230 may input or output signals, data, or information. In some embodiments, the I/O 230 may enable user interaction with the processing device 140. In some embodiments, the I/O 230 may include an input device and an output device.

The communication port 240 may be connected to a network (e.g., the network 120) to facilitate data communications. The communication port 240 may establish connections between the processing device 140 and the imaging device 110, the terminal device 130, or the storage device 150. The connection may be a wired connection, a wireless connection, or combination of both that enables data transmission and reception.

It should be noted that the above description of the computing device 200 is merely provided for the purposes of illustration, and not intended to limit the scope of the present disclosure. For persons having ordinary skills in the art, multiple variations and modifications may be made under the teachings of the present disclosure.

Figure 3:
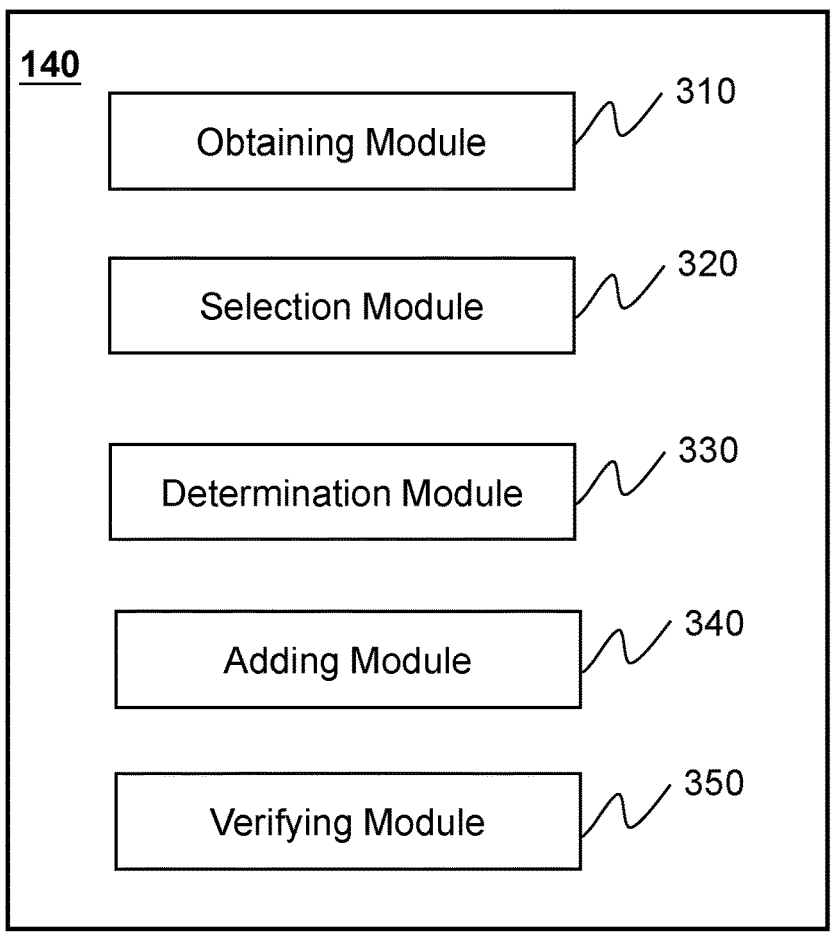
FIG. 3 is a block diagram illustrating an exemplary processing device according to some embodiments of the present disclosure.

FIG. 3 is a block diagram illustrating exemplary processing device 140 according to some embodiments of the present disclosure.

As shown in FIG. 3, the processing device 140 may include an obtaining module 310, a selection module 320, a determination module 330, and an adding module 340. As described in FIG. 1, the medical system 100 in the present disclosure may also include multiple processing devices, and the obtaining module 310, the selection module 320, the determination module 330, and the adding module 340 may be components of different processing devices.

The obtaining module 310 may be configured to obtain information relating to the medical system 100. For example, the obtaining module 310 may obtain sample images and annotation information of each of the sample images. each of the sample images may include one or more annotations, and the annotation information of each of the sample images may relate to the one or more annotations included in the sample image. More descriptions regarding the obtaining of the sample images and the annotation information of each of the sample images may be found elsewhere in the present disclosure. See, e.g., operation 410 in FIG. 4, and relevant descriptions thereof.

The selection module 320 may be configured to select one or more candidate sample images from the sample images based on feature information of a target image to be annotated. A candidate sample image refers to a sample image selected from the sample images that has similar feature information to the target image. More descriptions regarding the selecting of the one or more candidate sample images may be found elsewhere in the present disclosure. See, e.g., operation 420 in FIG. 4, and relevant descriptions thereof.

The determination module 330 may be configured to determine target annotation information of one or more target annotations to be added to the target image based on the annotation information of the one or more candidate sample images. In some embodiments, the target annotation information may include an annotation number, an annotation time of each target annotation, an annotation text of each target annotation, a type of each target annotation, an annotation position of each target annotation, or the like, or any combination thereof. More descriptions regarding the determination of the target annotation information may be found elsewhere in the present disclosure. See, e.g., operation 430 in FIG. 4, and relevant descriptions thereof.

The adding module 340 may be configured to add the one or more target annotations to the target image based on the target annotation information. More descriptions regarding the adding of the one or more target annotations to the target image may be found elsewhere in the present disclosure. See, e.g., operation 440 in FIG. 4, and relevant descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, any one of the modules may be divided into two or more units. For instance, the obtaining module 310 may be divided into two units configured to acquire different data. In some embodiments, the processing device 140 may include one or more additional modules, such as a storage module (not shown) for storing data.

FIG. 4 is a flowchart illustrating an exemplary process 400 for image annotation according to some embodiments of the present disclosure.

The image annotation may be performed on a target image to be annotated. The target image may be a medical image (e.g., a CT image, an MRI image, an ultrasound image, etc.) collected by the imaging device 110.

In 410, the processing device 140 (e.g., the obtaining module 310) may obtain sample images and annotation information of each of the sample images, each of the sample images including one or more annotations, and the annotation information of each of the sample images relating to the one or more annotations included in the sample image.

In some embodiments, the sample images may be of the same type as the target image. As used herein, if two images are acquired using the same imaging modality, the two images are deemed as being of the same type. For example, all the sample images and the target image may be ultrasound images. In some embodiments, the sample images may be medical images obtained within a preset historical time period. The historical time period may be set manually by a user (e.g., an engineer) according to an experience value or a default setting of the medical system 100. For example, the historical time period may be a period of time back from the current time.

In some embodiments, an annotation of an image may be used to mark and describe a region of interest (ROI) (e.g., an organ, a tissue, a lesion, etc.) in the image. For example, two annotations "Left Kidney" and "Right Kidney" may be added to specific locations in the image to mark the left kidney and right kidney in the image. The one or more annotations may be added manually by a user (e.g., a radiologist). Alternatively, the one or more annotations may be added automatically. Optionally, the one or more annotations added automatically may be confirmed (or modified) by a user.

In some embodiments, the annotation information of each sample image may include an annotation number, an annotation time of each annotation included in the sample image, an annotation text of each annotation included in the sample image, a type of each annotation included in the sample image, an annotation position of each annotation included in the sample image, or the like, or any combination thereof. The annotation number refers to a count of the one or more annotations included in the sample image. An annotation time of an annotation refers to a time when the annotation is added to the sample image. A type of an annotation may include a general annotation, a special annotation, etc. The general annotation refers to an annotation on a common structure (e.g., an organ or tissue) of subjects (e.g., human). The special annotation refers to an annotation on a specific structure (e.g., a lesion) of the subject. An annotation position of an annotation refers to a position of the annotation in the sample image. The annotation text of an annotation refers to text included the annotation for describing the corresponding ROI.

In some embodiments, the sample images and the annotation information of each sample image may be previously generated and stored in a storage device (e.g., the storage device 150, the storage 220, or an external source). The processing device 140 may retrieve the sample images and the annotation information of each sample image directly from the storage device.

In some embodiments, at least a portion of the annotation information of a sample image may be obtained by an annotation information determination model. For example, the annotation information determination model may be a text recognition model for recognizing texts in an image. Specifically, the sample image may be input into the text recognition model, and the text recognition model may output the annotation number, the annotation position and the corresponding annotation text of each annotation included in the sample image. In some embodiments, the text recognition model may include a machine learning model (e.g., a deep learning model). Exemplary deep learning models may include a convolutional recurrent neural network (CRNN) model, a segment-based visual transformer with reinforcement learning (SVTR) model, a deep neural network (DNN) model, a convolutional Neural Network (CNN) model, a recurrent neural network (RNN) model, a feature pyramid network (FPN) model, a generative adversarial network (GAN) model, or the like, or any combination thereof.

In some embodiments, the processing device 140 may obtain the text recognition model from one or more components of the medical system 100 (e.g., the storage device 150, the terminals(s) 130) or an external source via a network (e.g., the network 120). For example, the text recognition model may be previously trained by a computing device (e.g., the processing device 140), and stored in a storage device (e.g., the storage device 150) of the medical system 100. The processing device 140 may access the storage device and retrieve the text recognition model.

In some embodiments, the text recognition model may be generated by training a preliminary model based on a plurality of training samples (also referred to as a plurality of first training samples). Each training sample may include a training image and reference annotation information corresponding to the training image, wherein the reference annotation information can be used as a ground truth (also referred to as a label) for model training. In some embodiments, the reference annotation information may be determined by a user or may be automatically determined by a training device.

The preliminary model may include one or more model parameters, such as the number (or count) of layers, the number (or count) of nodes, a loss function, or the like, or any combination thereof. Before training, the preliminary model may have one or more initial parameter values of the model parameter(s).

The training of the preliminary model may include one or more iterations to iteratively update the model parameters of the preliminary model based on the training sample(s) until a termination condition is satisfied in a certain iteration. Exemplary termination conditions may be that the value of a loss function obtained in the certain iteration is less than a threshold value, that a certain count of iterations has been performed, that the loss function converges such that the difference of the values of the loss function obtained in a previous iteration and the current iteration is within a threshold value, etc. The loss function may be used to measure a discrepancy between annotation information predicted by the preliminary model in an iteration and the reference annotation information. For example, the training image of each training sample may be inputted into the preliminary model, and the preliminary model may output predicted annotation information of the training image. The loss function may be used to measure a difference between the predicted annotation information and the reference annotation information of each training sample. Exemplary loss functions may include a focal loss function, a log loss function, a cross-entropy loss, a Dice ratio, or the like. If the termination condition is not satisfied in the current iteration, the processing device 140 may further update the preliminary model to be used in a next iteration according to, for example, a backpropagation algorithm. If the termination condition is satisfied in the current iteration, the processing device 140 may designate the preliminary model in the current iteration as the text recognition model.

In 420, the processing device 140 (e.g., the selection module 320) may select, based on feature information of the target image to be annotated, one or more candidate sample images from the sample images.

A candidate sample image refers to a sample image selected from the sample images that has similar feature information to the target image.

In some embodiments, for each sample image, the processing device 140 may determine a similarity degree between the sample image and the target image based on sample feature information of the sample image and the feature information of the target image. In response to determining that the similarity degree exceeds a first similarity threshold, the processing device 140 may designate the sample image as one of the one or more candidate sample images. The first similarity threshold may be set manually by a user (e.g., an engineer) according to an experience value or a default setting of the medical system 100, or determined by the processing device 140 according to an actual need, such as 90%, 95%, or a larger or smaller value.

In some embodiments, the feature information of the target image may include one or more image features of the target image. Accordingly, the sample feature information of a sample image may include one or more image features of the sample image. Exemplary image features may include an RGB pixel value, a grayscale, a resolution, or the like, or any combination thereof. For example, the feature information may include a first vector including RGB pixel value of each pixel point in the target image, the sample feature information may include a second vector including RGB pixel value of each pixel point in the sample image, and a similarity degree between the first vector and the second vector may be determined as the similarity degree between the sample image and the target image. As another example, for each pixel in the target image, the processing device 140 may determine a difference between the RGB pixel value of the pixel in the target image and the RGB pixel value of a corresponding pixel in the sample image. In response to determining that the difference is smaller than an RGB threshold, the processing device 140 may designate the pixel as a similar pixel. The processing device 140 may designate a ratio of a count of the similar pixels to a total count of the pixels as the similarity degree.

In some embodiments, the sample images and the target image may be ultrasound images. The feature information may include one or more first operation parameters of a first ultrasound probe that collects the target image. The sample feature information of each sample image may include one or more second operation parameters of a second ultrasound probe that collects the sample image. In some embodiments, the first ultrasound probe and the second ultrasound probe may be the same ultrasound probe or different ultrasound probes. In some embodiments, exemplary operation parameters of an ultrasound probe may include a type, an imaging angle, an imaging mode (e.g., an amplitude mode, a brightness mode, a motiontype mode, a doppler mode, etc.) For example, the processing device 140 may determine an angle difference between a first imaging angle of the first ultrasound probe and a second imaging angle of the second ultrasound probe. The processing device 140 may determine a ratio of the angle difference to the first imaging angle. Further, the processing device 140 may determine the similarity degree based on the ratio. The higher the ratio, the smaller the similarity degree.

It should be noted that the above descriptions of the determination of the similarity degree are provided for illustration purposes, and not intended to be limiting. In some embodiments, the similarity degree may be determined based on both the image feature(s) of the sample image, the image feature(s) of the target image, the first operation parameter(s), and the second operation feature(s).

The one or more candidate sample images may be selected from the sample images to reduce the number of sample images used for determining the subsequent reference sample image, thereby improving the efficiency of the determination of the subsequent reference sample image, in turn improving the efficiency of adding target annotations for the target image.

In 430, the processing device 140 (e.g., the determination module 330) may determine target annotation information of one or more target annotations to be added to the target image based on the annotation information of the one or more candidate sample images.

In some embodiments, the target annotation information may be similar to the annotation information of the sample image. For example, the target annotation information may include an annotation number, an annotation time of each target annotation, an annotation text of each target annotation, a type of each target annotation, an annotation position of each target annotation, or the like, or any combination thereof.

In some embodiments, the processing device 140 may determine a reference sample image from the one or more candidate sample images. Further, the processing device 140 may determine the target annotation information based on the annotation information of the reference sample image. More descriptions regarding the determination of the target annotation information may be found elsewhere in the present disclosure (e.g., FIG. 5 and the descriptions thereof).

In 440, the processing device 140 (e.g., the adding module 340) may add the one or more target annotations to the target image based on the target annotation information.

In some embodiments, the processing device 140 may directly add the one or more target annotations to the target image based on the target annotation information. For example, for each target annotation, the processing device 140 may directly add the annotation text of the target annotation to an annotation position of the target annotation in the target image. In some embodiments, if a target annotation is the general annotation, the processing device 140 may directly add the annotation text of the target annotation to the annotation position of the target annotation in the target image. If a target annotation is the special annotation, the processing device 140 may send prompt information to a user, and the user may determine whether the target annotation needs to be added into the target image. In response to determining that the target annotation needs to be added into the target image, the processing device 140 may add the annotation text of the target annotation to the annotation position of the target annotation in the target image.

In some embodiments, the processing device 140 may verify whether the target annotation information satisfies a preset condition. In response to determining that the target annotation information satisfies the preset condition, the processing device 140 may add the one or more target annotations to the target image based on the target annotation information.

In some embodiments, the processing device 140 may determine, from the sample images, one or more verification sample images other than the reference sample image based on the annotation information of each sample image and the target annotation information. A verification sample image refers to a sample image selected from the sample images that includes similar annotations to the one or more target annotations. For example, if the one or more target annotations include three annotations with annotation text A, B, and C, respectively, the processing device 140 may determine one or more sample images, which also include three annotations with the annotation text A, B, and C, respectively, as the verification sample image(s).

Further, the processing device 140 may verify whether the target annotation information satisfies a preset condition based on the one or more verification sample images. In some embodiments, the preset condition may relate to the similarity degree between each verification sample image and the target image. Specifically, for each verification sample image, the processing device 140 may determine a similarity degree between the verification sample image and the target image based on sample feature information of the verification sample image and the feature information of the target image. In some embodiments, the determination of the similarity degree between a verification sample image and the target image may be performed in a similar manner as that of the similarity degree between a sample image and the target image described in operation 420, and the descriptions thereof are not repeated here. Further, the processing device 140 may verify whether the target annotation information satisfies the preset condition based on the similarity degree between each verification sample image and the target image. For example, the processing device 140 may determine whether a count of verification sample images whose similarity degrees exceed a second similarity threshold is greater than a count threshold. For brevity, the one or more verification sample images whose similarity degrees exceed the second similarity threshold may be also referred to as one or more target verification sample images. In response to determining that the count of the one or more target verification sample images is greater than the count threshold, the processing device 140 may determine that the target annotation information satisfies the preset condition. As another example, the processing device 140 may determine an average similarity degree of the similarity degrees corresponding to the one or more verification sample images. In response to determining that the average similarity is greater than a third similarity threshold, the processing device 140 may determine that the target annotation information satisfies the preset condition.

In some embodiments, for each of one or more of the one or more target annotations, the processing device 140 may verify whether the annotation position of the target annotation needs to be adjusted based on the one or more target verification sample images. Specifically, the processing device 140 may determine an average annotation position according to the annotation position of the corresponding annotation included in each target verification sample image. Then, the processing device 140 may determine whether a distance between the annotation position of the target annotation and the average annotation position is smaller than a distance threshold. In response to determining that the distance between the annotation position of the target annotation and the average annotation position is smaller than the distance threshold, the processing device 140 may determine that the annotation position of the target annotation does not need to be adjusted. In response to determining that the distance between the annotation position of the target annotation and the average annotation position is not smaller than the distance threshold, the processing device 140 may determine that the annotation position of the target annotation needs to be adjusted, and adjust the annotation position of the target annotation based on the average annotation position. For example, the processing device 140 may adjust the annotation position of the target annotation to the average annotation position.

The second similarity threshold, the third similarity threshold, or the distance threshold may be set manually by a user (e.g., an engineer) according to an experience value or a default setting of the medical system 100, or determined by the processing device 140 according to an actual need.

In some embodiments, in response to determining that the target annotation information does not satisfy the preset condition, the processing device 140 may obtain a new reference sample image, update the one or more target annotations based on the new reference sample image, and further add the one or more updated target annotations to the target image based on the updated target annotation information. Alternatively, in response to determining that the target annotation information does not satisfy the preset condition, the processing device 140 may update the target annotation information based on the annotation information of the one or more verification sample images or the one or more target verification sample images.

In some embodiments, the target annotation information may need to be confirmed or verified by a user before the one or more target annotations are added to the target image. In some embodiments, the target annotation information may be adjusted by a user. For example, the text annotations of the one or more target annotations may be edited, moved, deleted, etc., by the user via a user terminal.

As described elsewhere in the present disclosure, according to the conventional image annotation approaches, one or more annotations are manually added to a medical image by a user, which is inefficient. Compared with the conventional image annotation approaches, the methods and systems of the present disclosure may be automatically implemented with reduced or minimal or without user intervention, which is more efficient by, e.g., reducing the workload of a user and the time needed for the image annotation. In addition, in some embodiments, the target annotation information may be verified before the one or more target annotations are added to the target image. Moreover, in some embodiments, the annotation positions of the target annotations may also be adjusted to determine more accurate annotation positions. In this way, the accuracy of the target annotation information may be improved, thereby improving the accuracy of the image annotation.

FIG. 5 is a flowchart illustrating an exemplary process 500 for determining target annotation information according to some embodiments of the present disclosure. In some embodiments, one or more operations of the process 500 may be performed to achieve at least part of operation 430 as described in connection with FIG. 4.

In 510, the processing device 140 (e.g., the determination module 330) may determine a reference sample image from the one or more candidate sample images.

The reference sample image refers to one sample image selected from the candidate sample image(s) used for determining the target annotation information.

In some embodiments, if there is only one candidate sample image, the processing device 140 may directly designate the candidate sample image as the reference sample image.

In some embodiments, if there are a plurality of candidate sample images, the processing device 140 may randomly select one candidate sample image from the plurality of candidate sample images as the reference sample image.

In some embodiments, the annotation information of each sample image may include the annotation number and/or the annotation time of each annotation included in the sample image. The processing device 140 may determine the reference sample image based on the annotation number and/or the annotation time of each candidate sample image. For example, the processing device 140 may directly determine the candidate sample image that has the largest annotation number among the candidate sample images, and designate the candidate sample image as the reference sample image. As another example, if there are a plurality of candidate sample images that have the largest annotation number, the processing device 140 may determine the candidate sample image that has the latest annotation time among the candidate sample images that have the largest annotation number, and designate the candidate sample image as the reference sample image. As still another example, the processing device 140 may directly determine the candidate sample image that has the latest annotation time among the candidate sample images, and designate the candidate sample image as the reference sample image.

In some embodiments, for each of the one or more candidate sample images, the processing device 140 may determine a reliability value of each annotation included in the candidate sample image based on the annotation information of the candidate sample image. The processing device 140 may further determine the reference sample image based on the reliability value of each annotation in each of the one or more candidate sample images. As used herein, a reliability value of an annotation included in the candidate sample image may indicate a reference value of the annotation for determining the target annotation information, that is, a credibility of the annotation being used as a target annotation to be added to the target image. Specifically, for each candidate sample image, the processing device 140 may determine a total reliability value of the candidate sample image based on the reliability value of each annotation included in the candidate sample image. For example, the processing device 140 may determine a sum of the one or more reliability values of the one or more annotations included in the candidate sample image as the total reliability value. As another example, the processing device 140 may determine an average (or a weighted average) of the one or more reliability values of the one or more annotations included in the candidate sample image as the total reliability value. Further, the processing device 140 may determine the reference sample image based on the total reliability value of each candidate sample image. For example, the processing device 140 may designate the candidate sample image with the maximum total reliability value as the reference sample image. In some embodiments, the processing device 140 may determine the reference sample image based on the total reliability value, the annotation number, and/or the annotation time of each candidate sample image. For example, the processing device 140 may determine one or more initial reference sample images whose total reliability values are greater than a reliability threshold from the one or more candidate sample images, and designate the initial reference sample image that has the latest annotation time among the one or more initial reference sample images as the reference sample image. As another example, the processing device 140 may determine one or more initial reference sample images whose total reliability values are greater than the reliability threshold from the one or more candidate sample images, and designate the initial reference sample image that has the largest annotation number as the reference sample image. As still another example, the processing device 140 may determine one or more initial reference sample images that have the largest annotation number from the one or more candidate sample images, and designate the initial reference sample image that has the maximum total reliability value as the reference sample image.

In some embodiments, for each annotation included in a candidate sample image, the processing device 140 may determine the type of the annotation based on the annotation information of the candidate sample image. Further, the processing device 140 may determine the reliability value of the annotation based on the type of the annotation. As described in operation 410, a type of an annotation may include a general annotation, a special annotation, etc. The general annotation refers to an annotation on a common structure (e.g., an organ or tissue) of subjects (e.g., human). The special annotation refers to an annotation on a specific structure (e.g., a lesion) of the subject. In some embodiments, the reliability value of the general annotation may be larger than the reliability value of the special annotation. In some embodiments, the reliability values of the general annotation and the special annotation may be previously set manually by a user (e.g., an engineer) according to an experience value or a default setting of the medical system 100, or determined by the processing device 140 according to an actual need. For example, the reliability value of the general annotation may be 0.8, and the reliability value of the special annotation may be 0.3.

In some embodiments, for each annotation included in a candidate sample image, the processing device 140 may obtain a priority of the annotation from an annotation library based on the annotation information of the candidate sample image. The annotation library may store annotations and their respective priorities. The annotation library may be constructed manually by a user according to experiences, or be constructed automatically by analyzing historical annotated images by a compute device. For example, the annotation library may be a table that includes multiple text annotations and their respective priorities. Optionally, the annotations in the annotation library are grouped into multiple groups, and the annotations in each group are ranked according to their priorities in a descending order. The processing device 140 may obtain the annotation text of the annotation from the annotation information of the candidate sample image. Then, the processing device 140 may retrieve the priority corresponding to the annotation text of the annotation from the annotation library.

Further, the processing device 140 may determine the reliability value of the annotation based on the priority of the annotation. In some embodiments, the higher the priority of the annotation is, the larger the reliability value of the annotation may be. In some embodiments, the reliability values corresponding to different priorities may be previously set manually by a user (e.g., an engineer) according to an experience value or a default setting of the medical system 100, or determined by the processing device 140 according to an actual need. For example, the reliability values corresponding to priorities 1-10 may be 0.1, 0.2, . . . , 0.9, and 1, respectively.

In 520, the processing device 140 (e.g., the determination module 330) may determine the target annotation information based on the annotation information of the reference sample image.

The annotation information of the reference sample image may include an annotation number, an annotation time of each annotation included in the reference sample image, an annotation text of each annotation included in the reference sample image, a type of each annotation included in the reference sample image, an annotation position of each annotation included in the reference sample image, or the like, or any combination thereof.

In some embodiments, the processing device 140 may designate the annotation number of the reference sample image as the annotation number of the target annotation information of the target image. Each of the one or more target annotations may correspond to one annotation included in the reference sample image. For each target annotation, the processing device 140 may designate the annotation text and the type of a corresponding annotation included in the reference sample image as the annotation text and the type of the target annotation.

In some embodiments, for each target annotation, the processing device 140 may designate the annotation position of a corresponding annotation included in the reference sample image as the annotation position of the target annotation. In some embodiments, for each target annotation, the processing device 140 may determine one or more reference candidate sample images each of which includes a corresponding annotation similar to the target annotation from the one or more candidate sample images. In some embodiments, the one or more reference candidate sample images may include the reference sample image. Further, the processing device 140 may determine the annotation position of a corresponding annotation included in each of one or more reference candidate sample images, and determine the annotation position of the target annotation by weighting the annotation positions of the corresponding annotations based on weights corresponding to the one or more reference candidate sample images. In some embodiments, for each sample image of the one or more reference candidate sample images, the processing device 140 may determine a ratio of the total reliability value corresponding to the sample image to a sum of the total reliability values corresponding to the one or more reference candidate sample images as a weight corresponding to the sample image.

In some embodiments, for each target annotation, the processing device 140 may determine an annotation position of the target annotation based on the annotation position of the corresponding annotation, a size of the reference sample image, and a size of the target image. In some embodiments, the processing device 140 may determine a size ratio of the size of the target image to the size of the reference sample image. It can be considered that a ratio between a coordinate of the annotation position of the target annotation and a coordinate of the annotation position of the corresponding annotation may be equal to the size ratio. Therefore, the processing device 140 may determine the annotation position of the target annotation according to the annotation position of the corresponding annotation and the size ratio. For example, if the size ratio is 1:2, the annotation position of the corresponding annotation is (30, 60), the processing device 140 may determine the annotation position of the target annotation may be (30/2, 60/2), i.e., (15, 30).

In some embodiments, the processing device 140 may generate a new reference sample image with the same size as the target image based on the size of the reference sample image and the size of the target image. Further, the processing device 140 may determine a new annotation position in the new reference sample image corresponding to the annotation position of the corresponding annotation. Then, the processing device 140 may the annotation position of the target annotation by registering the new reference sample image and the target image.

In some embodiments, the sample images and the target image may be ultrasound images. The processing device 140 may determine one or more first operation parameters of a first ultrasound probe that collects the target image and one or more second operation parameters of a second ultrasound probe that collects the reference sample image. The processing device 140 may determine a pseudo image corresponding to the one or more first operation parameters based on the one or more first operation parameters and the one or more second operation parameters. The pseudo image may be regarded as a predicted image that is collected using the one or more first operation parameters. The processing device 140 may further determine a reference position in the pseudo image corresponding to the annotation position of the corresponding annotation, and determine the annotation position of the target annotation based on the reference position, the size of the reference sample image, and the size of the target image.

In some embodiments, exemplary operation parameters of an ultrasound probe may include a type, an imaging angle, an imaging mode (e.g., an amplitude mode, a brightness mode, a motiontype mode, a doppler mode, etc.). For illustration purposes, the imaging angle is described hereinafter as an exemplary operation parameter. In some embodiments, the processing device 140 may transform the reference sample image into a three-dimensional (3D) image, and determine a projection image corresponding to the first imaging angle of the first ultrasound probe as the pseudo image.

In some embodiments, the processing device 140 may determine the pseudo image using an image transforming model. The image transforming model may be a trained model (e.g., a machine leaning model) for transforming ultrasound images corresponding to different imaging angles (and/or other operation parameters). Specifically, the reference sample image, the second imaging angle corresponding to the reference sample image, and the first imaging angle may be input into the image transforming model, and the image transforming model may output the pseudo image corresponding to the first imaging angle. In some embodiments, the image transforming model may include a deep learning model, such as a deep neural network (DNN) model, a convolutional Neural Network (CNN) model, a recurrent neural network (RNN) model, a feature pyramid network (FPN) model, a generative adversarial network (GAN) model, or the like, or any combination thereof.

In some embodiments, the processing device 140 may obtain the image transforming model in a similar manner as how the text recognition model is obtained. In some embodiments, the image transforming model may be generated based on a plurality of second training samples. Each second training sample may include a first sample image of a subject collected by a first sample ultrasound probe, a first sample imaging angle of the first sample ultrasound probe that collects the first sample image, a second sample image of the subject collected by a second sample ultrasound probe, a second sample imaging angle of the second sample ultrasound probe that collects the reference sample image, wherein the second sample image can be used as a ground truth (also referred to as a label) for model training. In some embodiments, the first sample ultrasound probe and the second sample ultrasound probe may the same sample ultrasound probe.

After the pseudo image is generated, the processing device 140 may determine the reference position in the pseudo image corresponding to the annotation position of the corresponding annotation. For example, the processing device 140 may determine the reference position in the pseudo image corresponding to the annotation position of the corresponding annotation by registering the pseudo image and the reference sample image.

It should be understood that a size of the pseudo image is the same as the size of the reference sample image. Further, the processing device 140 may determine the annotation position of the target annotation based on the reference position, the size of the reference sample image, and the size of the target image. In some embodiments, the processing device 140 may determine the annotation position of the target annotation based on the reference position, the size of the reference sample image, and the size of the target image in a similar manner as how the annotation position of the target annotation is determined based on the annotation position of the corresponding annotation, the size of the reference sample image, and the size of the target image, and the descriptions thereof are not repeated here.

It can be understood that image differences between ultrasound images may be caused by using different operation parameters (e.g., different imaging angles). According to some embodiments of the present disclosure, the processing device 140 may transform the reference sample image into the pseudo image that corresponds to the same operation parameter(s) (e.g., the same imaging angle) as the target image, and further determine the annotation position of the target annotation based on the pseudo image. In this way, the effect of the different operation parameters may be eliminated or reduced, which may improve the accuracy of the determination of the annotation position of the target annotation.

In some embodiments, for a general annotation of the one or more target annotations, the processing device 140 may determine the ROI (e.g., an organ or a tissue) marked and described by the general annotation. The processing device

140 may determine a region in the target image corresponding to the ROI using an algorithm such as an image recognition algorithm. Then, the processing device 140 may determine a position that is located near the region in the target image as the annotation position of the general annotation.

It should be noted that the processes 400 and 500 and the descriptions thereof are provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure. For example, the operations of the illustrated processes 400 and 500 are intended to be illustrative. In some embodiments, the processes 400 and 500 may be accomplished with one or more additional operations not described, and/or without one or more of the operations discussed. Additionally, the order in which the operations of the processes 400 and 500 and regarding descriptions are not intended to be limiting.

Figure 6:
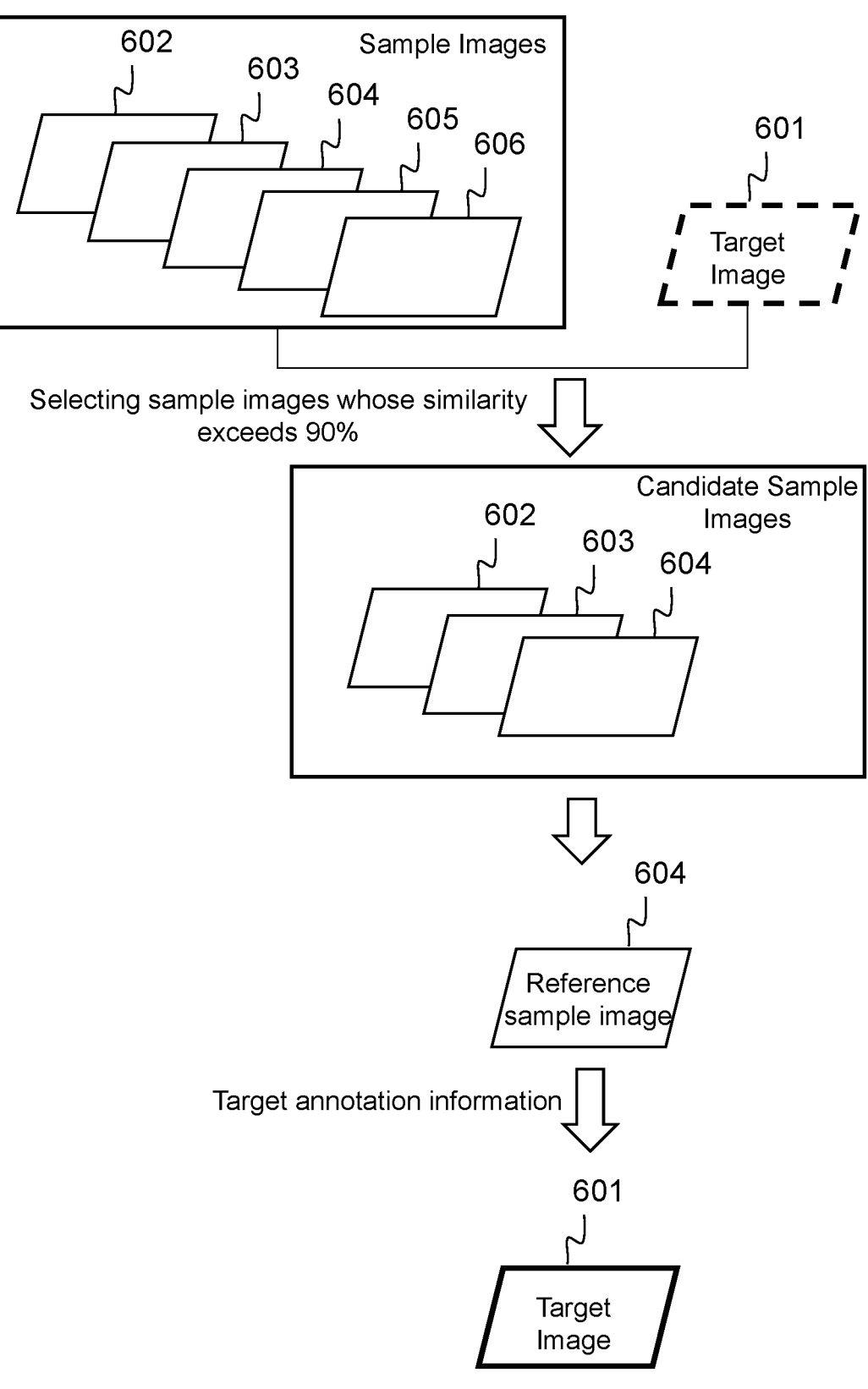
FIG. 6 is a schematic diagram illustrating an exemplary process for image annotation according to some embodiments of the present disclosure.

FIG. 6 is a schematic diagram illustrating an exemplary process 600 for image annotation according to some embodiments of the present disclosure. As shown in FIG. 6, a target image 601 needs to be annotated. The processing device 140 obtains sample images 602-606 and annotation information of each of the sample images 602-606. For each of the sample images 602-606, the processing device 140 determines a similarity degree between the sample image and the target image 601. The processing device 140 selects the sample images 602-604 whose similarity degrees exceed 90% as candidate sample images. Then, the processing device 140 determines a reference sample image 604 from the candidate sample images 602-604. Further, the processing device 140 determines target annotation information of one or more target annotations to be added to the target image 601 based on the annotation information of the reference sample image 604, and adds the one or more target annotations to the target image 601 based on the target annotation information.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an subject oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable. In some embodiments, a classification condition used in classification or determination is provided for illustration purposes and modified according to different situations. For example, a classification condition that "a value is greater than the threshold value" may further include or exclude a condition that "the probability value is equal to the threshold value."

What is claimed is:

1. A system for image annotation, comprising:
at least one storage device including a set of instructions; and
at least one processor in communication with the at least one storage device, wherein when executing the set of instructions, the at least one processor is configured to direct the system to perform operations including:
obtaining sample images and annotation information of each of the sample images, each of the sample images including one or more annotations, and the annotation information of each of the sample images relating to the one or more annotations included in the sample image;
selecting, based on feature information of a target image to be annotated, one or more candidate sample images from the sample images;
determining target annotation information of one or more target annotations to be added to the target image based on the annotation information of the one or more candidate sample images; and
adding the one or more target annotations to the target image based on the target annotation information.

2. The system of claim 1, wherein the selecting, based on feature information of a target image to be annotated, one or more candidate sample images from the sample images includes:
for each of the sample images,
determining a similarity degree between the sample image and the target image based on sample feature information of the sample image and the feature information of the target image; and
in response to determining that the similarity degree exceeds a threshold, designating the sample image as one of the one or more candidate sample images.

3. The system of claim 2, wherein
the sample images and the target image are ultrasound images,
the feature information includes one or more first operation parameters of a first ultrasound probe that collects the target image, and
the sample feature information of each sample image includes one or more second operation parameters of a second ultrasound probe that collects the sample image.

4. The system of claim 1, wherein the determining target annotation information of one or more target annotations to be added to the target image based on the annotation information of the one or more candidate sample images includes:
determining a reference sample image from the one or more candidate sample images; and
determining the target annotation information based on the annotation information of the reference sample image.

5. The system of claim 4, wherein
the annotation information of each of the sample images includes an annotation number and/or an annotation time of each annotation included in the sample image, and
the reference sample image is the candidate sample image that has the largest annotation number and/or the latest annotation time among the one or more candidate sample images.

6. The system of claim 4, wherein the determining a reference sample image from the one or more candidate sample images includes:
for each of the one or more candidate sample images, determining a reliability value of each annotation included in the candidate sample image based on the annotation information of the candidate sample image; and
determining the reference sample image based on the reliability value of each annotation in each of the one or more candidate sample images.

7. The system of claim 6, wherein the determining a reliability value of each annotation included in the candidate sample image based on the annotation information of the candidate sample image includes:
for each annotation included in the candidate sample image,
obtaining, based on the annotation information of the candidate sample image, a priority of the annotation from an annotation library, the annotation library storing annotations and their respective priorities; and
determining, based on the priority of the annotation, the reliability value of the annotation.

8. The system of claim 4, wherein the annotation information of the reference sample image includes annotation text and an annotation position of each annotation included in the reference sample image, and the determining the target annotation information based on the annotation information of the reference sample image includes:
for each of the one or more target annotations,
designating the annotation text of a corresponding annotation included in the reference sample image as an annotation text of the target annotation; and determining an annotation position of the target annotation based on the annotation position of the corresponding annotation, a size of the reference sample image, and a size of the target image.

9. The system of claim 8, wherein the sample images and the target image are ultrasound images, and the determining an annotation position of the target annotation includes:

determining one or more first operation parameters of a first ultrasound probe that collects the target image and one or more second operation parameters of a second ultrasound probe that collects the reference sample image;

determining, based on the one or more first operation parameters and the one or more second operation parameters, a pseudo image corresponding to the reference sample image;

determining a reference position in the pseudo image corresponding to the annotation position of the corresponding annotation; and determining the annotation position of the target annotation based on the reference position, the size of the reference sample image, and the size of the target image.

10. The system of claim 4, wherein the adding the one or more target annotations to the target image based on the target annotation information includes:

determining, from the sample images, one or more verification sample images other than the reference sample image based on the annotation information of each of the sample images and the target annotation information;

verifying, based on the one or more verification sample images, whether the target annotation information satisfies a preset condition; and in response to determining that the target annotation information satisfies the preset condition, adding the one or more target annotations to the target image based on the target annotation information.

11. A method for image annotation, the method being implemented on a computing device having at least one storage device and at least one processor, the method comprising:

obtaining sample images and annotation information of each of the sample images, each of the sample images including one or more annotations, and the annotation information of each of the sample images relating to the one or more annotations included in the sample image;

selecting, based on feature information of a target image to be annotated, one or more candidate sample images from the sample images;

determining target annotation information of one or more target annotations to be added to the target image based on the annotation information of the one or more candidate sample images; and adding the one or more target annotations to the target image based on the target annotation information.

12. The method of claim 11, wherein the selecting, based on feature information of a target image to be annotated, one or more candidate sample images from the sample images includes:

for each of the sample images, determining a similarity degree between the sample image and the target image based on sample feature information of the sample image and the feature information of the target image; and in response to determining that the similarity degree exceeds a threshold, designating the sample image as one of the one or more candidate sample images.

13. The method of claim 12, wherein the sample images and the target image are ultrasound images, the feature information includes one or more first operation parameters of a first ultrasound probe that collects the target image, and the sample feature information of each sample image includes one or more second operation parameters of a second ultrasound probe that collects the sample image.

14. The method of claim 11, wherein the determining target annotation information of one or more target annotations to be added to the target image based on the annotation information of the one or more candidate sample images includes:

determining a reference sample image from the one or more candidate sample images; and determining the target annotation information based on the annotation information of the reference sample image.

15. The method of claim 14, wherein the annotation information of each of the sample images includes an annotation number and/or an annotation time of each annotation included in the sample image, and the reference sample image is the candidate sample image that has the largest annotation number and/or the latest annotation time among the one or more candidate sample images.

16. The method of claim 14, wherein the determining a reference sample image from the one or more candidate sample images includes:

for each of the one or more candidate sample images, determining a reliability value of each annotation included in the candidate sample image based on the annotation information of the candidate sample image; and determining the reference sample image based on the reliability value of each annotation in each of the one or more candidate sample images.

17. The method of claim 16, wherein the determining a reliability value of each annotation included in the candidate sample image based on the annotation information of the candidate sample image includes:

for each annotation included in the candidate sample image, obtaining, based on the annotation information of the candidate sample image, a priority of the annotation from an annotation library, the annotation library storing annotations and their respective priorities; and determining, based on the priority of the annotation, the reliability value of the annotation.

18. The method of claim 14, wherein the annotation information of the reference sample image includes annotation text and an annotation position of each annotation included in the reference sample image, and the determining the target annotation information based on the annotation information of the reference sample image includes:

for each of the one or more target annotations, designating the annotation text of a corresponding annotation included in the reference sample image as an annotation text of the target annotation; and determining an annotation position of the target annotation based on the annotation position of the corresponding annotation, a size of the reference sample image, and a size of the target image.

19. The method of claim 18, wherein the sample images and the target image are ultrasound images, and the determining an annotation position of the target annotation includes:

determining one or more first operation parameters of a first ultrasound probe that collects the target image and one or more second operation parameters of a second ultrasound probe that collects the reference sample image;

determining, based on the one or more first operation parameters and the one or more second operation parameters, a pseudo image corresponding to the one or more first operation parameters;

determining a reference position in the pseudo image corresponding to the annotation position of the corresponding annotation; and determining the annotation position of the target annotation based on the reference position, the size of the reference sample image, and the size of the target image.

20. A non-transitory computer readable medium, comprising at least one set of instructions for image annotation, wherein when executed by one or more processors of a computing device, the at least one set of instructions causes the computing device to perform a method, the method comprising:

obtaining sample images and annotation information of each of the sample images, each of the sample images including one or more annotations, and the annotation information of each of the sample images relating to the one or more annotations included in the sample image;

selecting, based on feature information of a target image to be annotated, one or more candidate sample images from the sample images;

determining target annotation information of one or more target annotations to be added to the target image based on the annotation information of the one or more candidate sample images; and adding the one or more target annotations to the target image based on the target annotation information.

* * * * *